*(12)* United States Patent
Hacker et al.

US008536094B2

*(10)* Patent No.: US 8,536,094 B2
*(45)* Date of Patent: *Sep. 17, 2013

(54) HERBICIDAL COMPOSITIONS FOR TOLERANT OR RESISTANT RICE CROPS

(75) Inventors: Erwin Hacker, Hochheim (DE); Hermann Bieringer, Eppstein (DE); Lothar Willms, Hofheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/403,134

(22) Filed: Mar. 31, 2003

(65) Prior Publication Data

US 2003/0186815 A1   Oct. 2, 2003

Related U.S. Application Data

(63) Continuation of application No. 09/813,556, filed on Mar. 21, 2001, now abandoned, which is a continuation of application No. 09/371,611, filed on Aug. 10, 1999, now abandoned.

(30) Foreign Application Priority Data

Aug. 13, 1998 (DE) .................................. 198 36 684

(51) Int. Cl.
*A01N 57/20* (2006.01)
*A01N 57/14* (2006.01)
*A01N 43/18* (2006.01)
*A01N 43/12* (2006.01)
*A01N 43/46* (2006.01)
*A01N 43/653* (2006.01)

(52) U.S. Cl.
USPC ........... 504/127; 504/128; 504/139; 504/140; 504/142; 504/143; 504/149; 568/14; 568/33

(58) Field of Classification Search
USPC ................. 504/127, 128, 130, 138, 139, 129, 504/131, 132, 133, 134, 135, 136, 137, 140, 504/142, 143, 149
See application file for complete search history.

(56) References Cited

U.S. PATENT DOCUMENTS

| | | | |
|---|---|---|---|
| 4,265,654 A | 5/1981 | Takematsu et al. | |
| 4,981,507 A * | 1/1991 | Jelich et al. | 504/241 |
| 5,094,945 A | 3/1992 | Comai | |
| 5,173,103 A * | 12/1992 | Yoshida et al. | 504/128 |
| 5,206,021 A * | 4/1993 | Dookhith et al. | 424/405 |
| 5,273,894 A | 12/1993 | Strauch et al. | |
| 5,276,268 A | 1/1994 | Strauch et al. | |
| 5,461,019 A | 10/1995 | Willms et al. | |
| 5,545,822 A | 8/1996 | Croughan | |
| 5,569,639 A | 10/1996 | Beestman | |
| 5,599,769 A | 2/1997 | Hacker et al. | |
| 5,633,434 A | 5/1997 | Schneider et al. | |
| H0017111 | 2/1998 | Smith, III | |
| 5,739,082 A | 4/1998 | Donn | |
| 5,843,866 A * | 12/1998 | Parker et al. | 504/360 |
| 5,851,952 A * | 12/1998 | Karp et al. | 504/251 |
| H0001785 H * | 2/1999 | Theodoridis | 504/243 |
| 5,872,078 A * | 2/1999 | Kuchikata et al. | 504/206 |
| 5,935,905 A | 8/1999 | Mito | |
| 5,945,379 A | 8/1999 | Dollinger et al. | |
| 5,968,873 A * | 10/1999 | Dahmen et al. | 504/128 |
| 6,013,605 A * | 1/2000 | Rees et al. | 504/221 |
| 6,087,305 A * | 7/2000 | Kober et al. | 504/362 |
| 6,114,286 A * | 9/2000 | Takano | 504/240 |
| 6,165,939 A * | 12/2000 | Agbaje et al. | 504/105 |
| 6,239,072 B1 * | 5/2001 | Flint et al. | 504/127 |
| 6,586,367 B2 * | 7/2003 | Lee et al. | 504/127 |

FOREIGN PATENT DOCUMENTS

| | | |
|---|---|---|
| CA | 1291344 | 10/1991 |
| CA | 2238377 | 6/1998 |
| DE | 2856260 | 7/1979 |
| DE | 19720367 | 11/1997 |
| DE | 19638887 | 3/1998 |
| DE | 19642082 | 4/1998 |

(Continued)

OTHER PUBLICATIONS

Sankula, 1997, Weed Technology, 662-666.*

(Continued)

*Primary Examiner* — Sreeni Padmanabhan
*Assistant Examiner* — Irina Neagu
(74) *Attorney, Agent, or Firm* — Frommer Lawrence & Haug LLP

(57) ABSTRACT

Herbicide combinations (A)+(B), if appropriate in the presence of safeners, with an effective content of
(A) broad-spectrum herbicides from the group
   (A1) glufosinate (salts) and related compounds
   (A2) glyphosate (salts) and related compounds such as sulfosate,
   (A3) imidazolinones such as imazethapyr, imazapyr, imazaquin, imazamox or their salts and
   (A4) herbicidal azoles from the group of the protoporphyrinogen oxidase inhibitors (PPO inhibitors) and
(B) one or more herbicides from the group consisting of
   (B0) one or more structurally different herbicides from the abovementioned group (A) or
   (B1) foliar- and soil-acting herbicides effective against selectively in rice monocotyledonous and dicotyledonous harmful plants (residual action) or
   (B2) herbicides which are effective selectively in rice against dicotyledonous harmful plants and/or sedges, and/or
   (B3) foliar-acting herbicides which are effective selectively in rice against monocotyledonous harmful plants, and/or
   (B4) foliar- and soil-acting herbicides which are effective selectively in rice against monocotyledonous harmful plants,
herbicides from several of groups (B0) to (B4) are suitable for controlling harmful plants in rice which consists of tolerant or resistant mutants or transgenic rice plants and the rice crops are tolerant to the herbicides (A) and (B), if appropriate in the presence of safeners, which are contained in the combination.

11 Claims, No Drawings

(56) References Cited

FOREIGN PATENT DOCUMENTS

| | | |
|---|---|---|
| DE | 19834629 | 12/1998 |
| EP | 0 115 673 A2 | 8/1984 |
| EP | 0 242 236 A1 | 10/1987 |
| EP | 0 242 246 A1 | 10/1987 |
| EP | 0252237 | 1/1988 |
| EP | 0 257 542 A2 | 3/1988 |
| EP | 0 275 957 A2 | 7/1988 |
| EP | 0 409 815 A1 | 1/1991 |
| EP | 0 812 540 | 12/1997 |
| EP | 0 812 540 A2 | 12/1997 |
| FR | 2769176 | 4/1999 |
| GB | 2 267 825 | 12/1993 |
| JP | 05320009 * | 2/1991 |
| JP | 06263610 * | 9/1994 |
| JP | 1997227314 | 9/1997 |
| WO | WO91/11517 | 8/1991 |
| WO | WO92/00377 | 1/1992 |
| WO | WO92/08353 | 5/1992 |
| WO | WO 95/34659 | 12/1995 |
| WO | WO-9622692 | 8/1996 |
| WO | WO 97/10714 | 3/1997 |
| WO | WO-9717852 | 5/1997 |
| WO | WO97/20807 | 6/1997 |
| WO | WO 97/31535 | 9/1997 |
| WO | WO97/36488 | 10/1997 |
| WO | WO 97/41218 | 11/1997 |
| WO | WO 97/48276 | 12/1997 |
| WO | WO98/09525 | 3/1998 |
| WO | WO98/20144 | 5/1998 |
| WO | WO/98/20144 | 5/1998 |
| WO | WO 98/24321 | 6/1998 |
| WO | WO99/13723 | 3/1999 |
| WO | WO 99/23886 | 5/1999 |
| WO | WO 99/45781 | 9/1999 |
| WO | WO99/52367 | 10/1999 |

OTHER PUBLICATIONS

Maramba, Allelopathy in Rice, p. 140.*
Weed control in rice document (Weed control in rice, p. 48, 1981).*
W09208353_Translation.*
Chemical Abstract, vol. 128, No. 7 (1988).
Database accession No. 1997-90914.
Database accession No. 1991-82186.
Database accession No. 1995-83003.
Database accession No. 1996-80951.
Database accession No. 1997-86486.
Database accession No. 1991-82194.
The Pesticide Manual, $10^{th}$ Edition, pp. 1335-1341.
Database accession No. 1996-81455.
Katzek et al., Zxuckerrube, vol. 47 pp. 217-220, 1998.
Sankula et al, "Influence of Ignite Applications and Tankmixes on Resistant Rice and Red Rice", Proc. South. Weed Sci. Soc. (48 Meet., 3, 1995).
Bollich, P.K., Sanders, D.E., "Non-Selective and Residual Herbicide Tankmixes in No-Till Rice", 1993 Southern Conservation Tillage Conference for Sustainable Agriculture, pp. 21-25, Jun. 1993.
Product Label (Crop Protection Reference $14^{th}$ Edition 1998) for FACET® 75 DF herbicide: a product of BASF; active ingredient quinclorac (3,7-dichloro-8-quinolinecarboxlic acid) published 1998.
Hilll, J.E. et al, "Weed control in Rice-97", California Rice Research Board $29^{th}$ Annual Report—A Summary of Research from 1997.
Kanter, D.G., Miller, T.C. "1997 Rice Variety Performance Trials", Mississippi State University Information Bulletin 327, Feb. 1998.
De Witt, J., Heier, J, Rose, V. "V-10029 80 WP a new post-emergence herbicide for California rice", Proc. Calif. Weed Sci. Soc. 49 (Meet 174), 1997.
Webster, E. et al, "Herbicide Evaluation in Arkansas Rice, 1996", Arkansas Agricultural Experiment Station Research series 457, pp. 139-143, 1997.
Wheeler, C. et al, Weed Control in Liberty—Tolerant Rice Research Studies—1996, Arkansas Agricultural Experiment Station Series 456, pp. 72-74, Jul. 1997.

Product sheet (Crop Protection with Chemicals 1998) for LIBERTY (lufosinate ammonium), manufactured by AgrEvo (now Bayer), published Feb. 1998.
Product Label (Crop Protection Reference $13^{th}$ Edition 1997) for Roundup® ULTRA herbicide; a product of active ingredient isopropylamine salt of glyphosate, published 1997.
Product Label (Crop Protection Reference $13^{th}$ Edition 1997) for SURPASS® EC herbicide; a product of Zeneca; active ingredient acetochlor, published 1997.
Product Label (Crop Protection Reference $13^{th}$ Edition 1997) for TOPNOTCH® herbicide; a product of Zeneca; active ingredient acetochlor, published 1997.
Lueschen, W.E. et al, "Herbicide Tank Mix Combinations for Weed Control in Roundup-Ready™ Soybean", WSSA Abstracts, vol. 37, Abstract #244, Feb. 1997.
Product Label (Crop Protection Reference $13^{th}$ Edition 1997) for HARNESS® herbicide; a product of Monsanto; active ingredient acetochlor, published 1997.
Product Label (Crop Protection Reference $14^{th}$ Edition 1998) for LIGHTNING™ herbicide; a product of American Cyanamid company; active ingredients imazethapyr and itnazapyr published 1998.
Product Sheet (Crop Protection with Chemicals 1998) for POAST ULTRA (sethoxydim), manufactured by BASF, published Feb. 1998.
Product Label (Crop Protection Reference $13^{th}$ Edition 1997) for Pursuit® Dg herbicide; a product of American Cyanamid company; active ingredient imazethapyr, published 1997.
Product Label (Crop Protection Reference $13^{th}$ Edition 1997) for Pursuit™PLUS EC herbicide; a product of American Cyanamid company; active ingredients imazethapyr and pendimethalin published 1997.
Product Label (Crop Protection Reference $13^{th}$ Edition 1997) for SCEPTER® herbicide; a product of American Cyanamid Company; active ingredient imazaquin, published 1997.
Product Label (Crop Protection Reference $13^{th}$ Edition 1997) for SCEPTER® 70DG herbicide; a product of American Cyanamid Company; active ingredient imazaquin; published 1997.
Product Label (Crop Protection Reference $13^{th}$ Edition 1997) for SCEPTER® O.T.® herbicide; a product of American Cyanamid Company; active ingredients imazaquin and acifluorfen; published 1997.
Product Label (Crop Protection Reference $13^{th}$ Edition 1997) for SQUADRON® herbicide; a product of American Cyanamid Company; active ingredients the ammonium salt of imazaquin and pendimethalin; published 1997.
Product Label (Crop Protection Reference $13^{th}$ Edition 1997) for STATUS™ herbicide; a product of American Cyanamid Company; active ingredient acifluorfen; published 1997.
Product Label (Crop Protection Reference $13^{th}$ Edition 1998) for STEEL™ herbicide; a product of American Cyanamid Company; active ingredients imazaquin, imazethapyr and pendimethalin; published 1998.
Kapusta, G., Autman, S.T. Curvey, S.E., "IT Corn Weed Control with Scepter/Pursuit Applied Preplant Incorporated, Preemergence, and Postemergence", 1996 Progress Report —Southern Illinois Universitey (1996).
Kapusta, G., Krausz, R.F., Chadbourne, E.S., "Postemergence Weed Control with Lightning Combinations in SS 797IT and Garst 8326 IT Corn Hybrids", 1997 Progress Report—Southern Illinois University (1997).
Helms, R.B. et al., "Efficacy of sulfentrazone + PRE herbicides for southern crabgrass [Digitaria ciliaris (Retz.) Koel] control", WSSA Abstracts, vol. 37, Abstract #264 (Feb. 1997).
Niekamp, J.W. et al., "Total Pre Weed Control Programs with Sulfentrazone in No-Till Soybeans", North Cent. Weed Sci. Soc. Proc. (51, p. 125, 1996).
Guscar, H.L. et al., "Sulfentrazone + Clomazone and Sulfentrazone + Chlorimuron-Ethyl: Summary of 1996 Soybean EUP/TT Program", North Cent. Weed Sci. Soc. Proc. (51, p. 137, 1996).
Durgan, B.R. et al., "Wild oat control in hard red spring wheat and barley with F8426 tank mixes at Crookston, MN —1997", 1997 Small Grain Research Reports.
R.N. Arnold, E.J. Gregory, A. Berrada; Res. Prog. Rep. West Soc. Weed Sci., 1996 Meet.; p. 54.

G.A. Wicks, A.R. Martin and G.E. Hanson, Weed Technology 1997, vol. 11, pp. 567-572.

D.A. Wall, Weed Technology 1995, vol. 9, pp. 610-616.

T.A. Bauer, K.A. Renner and D. Penner; Weed Technology 1995, vol. 9, pp. 236-242.

B.W. Minton, D.R. Shaw and M.E. Kurtz; Weed Technology 1989, vol. 3, pp. 329-334.

L.B. McCarthy, J.M. Higgins and D.L. Colvin, Weed Technology 1993, vol. 7, pp. 911-915.

C. Tomlin (Ed.) The Pesticide Manual, $13^{th}$ Edition 2003, p. 1022.

J.M. Lich, K.A. Renner, D. Penner, Weed Science, vol. 45, pp. 12-21.

S. Sankula, M.P. Braverman, S.D. Linscombe, Proc. South Weed Sci. Soc. (48. Meet., p. 3) 1995.

R.T. Meister, Farm Chemicals Handbook 1995, vol. 81, Mesiter Publishing Company 1995; S. A2I, A37, A44, A59, C160, C11.

* cited by examiner

HERBICIDAL COMPOSITIONS FOR TOLERANT OR RESISTANT RICE CROPS

This application is a continuation of application Ser. No. 09/813,556, now abandoned, which was filed on Mar. 21, 2001, which in turn is a continuation of application Ser. No. 09/371,611 filed Aug. 10, 1999, now abandoned.

The invention is in the field of the crop protection products which can be employed against harmful plants in tolerant or resistant crops of rice and which comprise, as herbicidally active substances, a combination of two or more herbicides.

The introduction of tolerant or resistant rice varieties and maize lines, in particular transgenic rice varieties and rice lines, adds novel active substances which per se are not selective in conventional rice varieties, to the conventional weed control system. The active substances are, for example, the known broad-spectrum herbicides such as glyphosate, sulfosate, glufosinate, bialaphos and imidazolinone herbicides [herbicides (A)], which can now be employed in the tolerant crops developed specifically for them. The efficacy of these herbicides against harmful plants in the tolerant crops is high, but depends—similarly to other herbicide treatments—on the nature of the herbicide employed, its application rate, the preparation in question, the harmful plants to be controlled, the climatic conditions, the soil conditions etc. Furthermore, the herbicides exhibit weak points (zero effect) against specific species of harmful plants. Another criterion is the duration of action, or the degradation rate of the herbicide. If appropriate, changes in the sensitivity of harmful plants, which may occur upon prolonged use of the herbicides or within a geographical limited area, must also be taken into consideration. The loss of action against individual plants can only be compensated for to some extent by higher application rates of the herbicides, if at all. Moreover, there is always a demand for methods to achieve the herbicidal effect with lower application rates of active substances. A lower application rate not only reduces the amount of an active substance required for application, but as a rule, also reduces the amount of formulation auxiliaries required. Both reduce the economic outlay and improve the eco-friendliness of the herbicide treatment.

One possibility for improving the use profile of a herbicide may consist in combining the active substance with one or more other active substances which contribute the desired additional properties. However, the combined use of a plurality of active substances does not infrequently lead to phenomena of a physical and biological incompatibility, for example lacking stability of a coformulation, decomposition of an active substance or antagonism of the active substances. In contrast, what is desired are combinations of active substances with a favorable profile of action, high stability and as synergistic an increased action as possible, which allows the application rate to be reduced in comparison with the individual application of the active substances to be combined.

Surprisingly, it has now been found that active substances from the group of the abovementioned broad-spectrum herbicides (A) in combination with other herbicides from group (A) and/or specific herbicides (B) interact especially favorably when they are employed in the rice crops which are suitable for the selective use of the first-mentioned herbicides.

The invention therefore relates to the use of herbicide combinations for controlling harmful plants in rice crops, wherein the herbicide combination in question has a synergistically active content of (A) a broad-spectrum herbicide from the group of the compounds consisting of
(A1) compounds of the formula (A1),

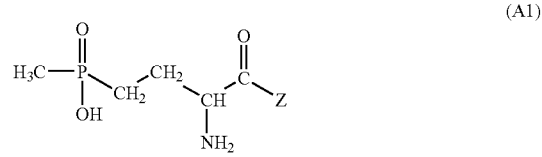

in which Z is a radical of the formula —OH or a peptide radical of the formula —NHCH(CH$_3$)CONHCH(CH$_3$)COOH or —NHCH(CH$_3$)CONHCH[CH$_2$CH(CH$_3$)$_2$]COOH, and their esters and salts, preferably glufosinate and its salts with acids and bases, in particular glufosinate-ammonium, L-glufosinate or its salts, bialaphos and its salts with acids and bases, and other phosphinothricin derivatives, (A2) compounds of the formula (A2) and their esters and salts,

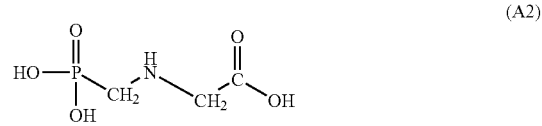

preferably glyphosate and its alkali metal salts or salts with amines, in particular glyphosate-isopropylammonium, and sulfosates, (A3) imidazolinones, preferably imazethapyr, imazapyr, imazamethabenz, imazamethabenz-methyl, imazaquin, imazamox, imazapic (AC 263,222) and their salts and (A4) herbicidal azoles from the protoporphyrinogen-oxidase inhibitors (PPO inhibitors), such as WC9717 (=CGA276854), and (B) one or more herbicides from the group of the compounds which consists of (B0) one or more structurally different herbicides from the abovementioned group (A) and/or (B1) foliar- and soil-acting herbicides which are effective selectively in rice against monocotyledonous and dicotyledonous harmful plants (residual action), and/or (B2) herbicides which are effective selectively in rice against dicotyledonous harmful plants and/or sedges, and/or (B3) foliar-acting herbicides which are effective selectively in rice against monocotyledonous harmful plants, and/or (B4) foliar- and soil-acting herbicides which are effective selectively in rice against monocotyledonous harmful plants, and the rice crops are tolerant to the herbicides (A) and (B) which form a constituent of the combination, if appropriate in the presence of safeners.

"Structurally different herbicides from the abovementioned group (A)" in group (B0) only include herbicides which are covered by the definition of group (A), but which are not component (A) in the combination in question.

In addition to the herbicide combinations according to the invention, other crop protection active substances and adjuvants and formulation auxiliaries conventionally used in crop protection may be used.

The synergistic effects are observed when the active substances (A) and (B) are applied together, but can also be observed upon split application (splitting). Another possibility is to apply the herbicides or herbicide combinations in several portions (sequential application), for example after pre-emergence applications, followed by post-emergence applications or after early post-emergence applications, followed by applications at medium or late post-emergence. Preferred is the simultaneous application of the active substances of the combination in question, if appropriate in several portions. However, a staggered application of the individual active substances of a combination is also possible and may be advantageous in individual cases. Other crop protection agents such as fungicides, insecticides, acaricides and the like, and/or different auxiliaries, adjuvants and/or fertilizer applications may also be integrated into this system application.

The synergistic effects allow the application rates of the individual active substances to be reduced, a more potent action against the same species of harmful plant combined with the same application rate, the control of species to which the action has hitherto not extended (zero effect), an extended application period and/or a reduced number of required individual applications and—as a result for the user—economical and ecologically more advantageous weed control systems.

For example, the combinations of (A)+(B) according to the invention allow synergistically increased effects which far and unexpectedly exceed the effects which can be achieved with the individual active substances (A) and (B).

WO-A-98/09525 has already described a method of controlling weeds in transgenic crops which are resistant to phosphorus-containing herbicides such as glufosinate or glyphosate, herbicide combinations being employed which comprise glufosinate or glyphosate and at least one herbicide from the group consisting of prosulfuron, primisulfuron, dicamba, pyridate, dimethenamid, metolachlor, flumeturon, propaquizafop, atrazine, clodinafop, norflurazone, ametryn, terbuthylazine, simazine, prometryn, NOA402989 (3-phenyl-4-hydroxy-6-chloropyridazine), a compound of the formula

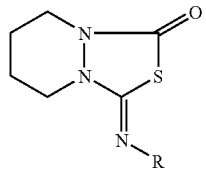

in which R=4-chloro-2-fluoro-5-(methoxycarbonylmethylthio)phenyl (disclosed in U.S. Pat. No. 4,671,819), CGA276854=1-allyloxycarbonyl-1-methylethyl 2-chloro-5-(3-methyl-2,6-dioxo-4-trifluoromethyl-3,6-dihydro-2H-pyrimidin-1-yl)-benzoate(=WC9717, disclosed in U.S. Pat. No. 5,183,492) and 4-oxetanyl 2-{N-[N-(4,6-dimethylpyrimidin-2-yl)aminocarbonyl]aminosulfonyl}benzoate (disclosed in EP-A-496701).

Details on the obtainable effects, or effects which have been obtained, cannot be found in the publication WO-A-98/09525. There are no examples on synergistic effects or on carrying out the method in specific crops, nor are there specific combinations of two, three or more herbicides.

DE-A-2856260 has already disclosed a few herbicide combinations with glufosinate or L-glufosinate and other herbicides such as alloxidim, linuron, MCPA, 2,4-D, dicamba, triclopyr, 2,4,5-T, MCPB and others.

Some herbicide combinations with glufosinate or glyphosate and other herbicides from the sulfonylurea series such as metsulfuron-methyl, nicosulfuron, primisulfuron, rimsulfuron and the like have already been disclosed in WO-A-92/083 53 and EP-A 0 252 237.

However, the use of the combinations for controlling harmful plants has been shown in the publications only with reference to a few plants species or else with reference to no example.

In our experiments, it has been found, surprisingly, that there exist large differences between the usefulness of the herbicide combinations mentioned in WO-A-98/09525 and in the other references and also of other novel herbicide combinations in crops of plants.

According to the invention, herbicide combinations which can be employed particularly advantageously in tolerant rice crops are provided.

The compounds of the formulae (A1) to (A4) are known or can be prepared analogously to known processes.

Formula (A1) encompasses all stereoisomers and their mixtures, in particular the racemate and the particular enantiomer which has a biological action, for example L-glufosinate and its salts. Examples of active substances of the formula (A1) are the following:

(A1.1) glufosinate in the narrow sense, i.e. D,L-2-amino-4-[hydroxy(methyl)-phosphinyl]butanoic acid,
(A1.2) glufosinate-monoammonium salt,
(A1.3) L-glufosinate, L- or (2S)-2-amino-4-[hydroxy(methyl)phosphinyl]butanoic acid (phosphinothricin),
(A1.4) L-glufosinate monoammonium salt,
(A1.5) bialaphos (or bilanafos), i.e. L-2-amino-4-[hydroxy-(methyl)phosphinyl]butanoyl-L-alanyl-L-alanine, in particular its sodium salt.

The abovementioned herbicides (A1.1) to (A1.5) are absorbed via the green parts of the plants and are known as broad-range herbicides or total herbicides; they are inhibitors of the enzyme glutamine synthetase in plants; see "The Pesticide Manual" 11th Edition, British Crop Protection Council 1997, pp. 643–645 and 120–121. While they can be employed post-emergence for controlling broad-leaved weeds and grass weeds in plantation crops and on non-crop area and, using specific application techniques, also for the in-between-rows treatment of agricultural ground crops such as maize, cotton and the like, the importance of use as selective herbicides in resistant transgenic crops of plants is increasing.

Glufosinate is usually employed in the form of a salt, preferably of the ammonium salt. The racemate of glufosinate, or glufosinate-ammonium, alone is usually applied at rates between 50 and 2000 g of a.s./ha, usually 200 and 2000 g of a.s./ha (=g of a.i./ha=grams of active substance per hectare). At such rates, glufosinate is effective mainly when taken up via the green parts of the plants.

However, since it is degraded microbially in the soil within a few days, it has no long-term action in the soil. The same also applies to the related active substance bialaphos sodium (also termed bilanafos-sodium); see "The Pesticide Manual" 11th Ed., British Crop Protection Council 1997 pp. 120–121.

As a rule, markedly less active substance (A1), for example an application rate in the range of 20 to 800, preferably 20 to 600, grams of active substance of glufosinate per hectare (g of a.s./ha or g of a.i./ha) is required in the combinations according to the invention. Similar amounts, preferably amounts which have been converted into moles per hectare, also apply to glufosinate-ammonium and bialafos, or bialafos-sodium.

The combinations with the foliar-acting herbicides (A1) are expediently employed in rice crops which are resistant or tolerant to the compounds (A1). Some tolerant rice crops which have been generated by genetic engineering, are already known and are employed in practice; cf. the article in the journal "Zuckerrübe" [Sugarbeet], year 47 (1998), p. 217 et seq.; for the generation of transgenic plants which are resistant to glufosinate, cf. EP-A-0242246, EP-A-242236, EP-A-257542, EP-A-275957, EP-A-0513054).

Examples of compounds (A2) are
(A2.1) glyphosate, i. e. N-phosphonomethyl)glycine,
(A2.2) glyphosate-monoisopropylammonium salt,
(A2.3) glyphosate-sodium salt,
(A2.4) sulfosate, i.e. N-(phosphonomethyl)glycine-trimesium salt=N-(phosphonomethyl)glycine-trimethylsulfoxonium salt.

Glyphosate is usually employed in the form of a salt, preferably of the monoisopropylammonium salt or the trimethylsulfoxonium salt (=trimesium salt=sulfosate). Based on the free acid glyphosate, the single dose is in the range of 0.050–5 kg of a.s./ha, usually 0.5–5 kg of a.s./ha. Glyphosate is similar to glufosinate with regard to certain applications, but, in contrast to the latter, it is an inhibitor of the enzyme 5-enolpyruvylshikimate-3-phosphate synthase in plants; see "The Pesticide Manual" 11th Ed., British Crop Protection Council 1997 pp. 646–649. In the combinations according to the invention, application rates in the range of 20 to 1000, preferably 20 to 800, g of a.s. glyphosate are, as a rule, required per ha.

Also, tolerant plants generated by genetic engineering are known for compounds (A2) and have been introduced into practice; cf. "Zuckerrübe" year 47 (1998), p. 217 et seq.; cf. also WO 92/00377, EP-A-1 15673, EP-A409815.

Examples of imidazolinone herbicides (A3) are
(A3.1) imazapyr and its salts and esters,
(A3.2) imazethapyr and its salts and esters,
(A3.3) imazamethabenz and its salts and esters,
(A3.4) imazamethabenz-methyl,
(A3.5) imazamox and its salts and esters,
(A3.6) imazaquin and its salts and esters, for example the ammonium salt,
(A3.7) imazapic (AC 263,222) and its salts and esters, for example the ammonium salt.

The herbicides inhibit the enzyme acetolactate synthase (ALS) and thus the protein synthesis in plants; they are both soil-acting and foliar-acting and, in some cases, show selectivities in crops; cf. "The Pesticide Manual" 11th Ed., British Crop Protection Council 1997 pp. 697–699 for (A3.1), pp. 701–703 for (A3.2), pp. 694–696 for (A3.3) and (A3.4), pp. 696–697 for (A3.5), pp. 699–701 for (A3.6) and pp. 5 and 6, reviewed as AC 263,222 (for A3.7). The application rates of the herbicides are usually between 0.01 and 2 kg of a.s./ha, usually 0.1 and 2 kg of a.s./ha. In the combinations according to the invention, they are in the range of 10 to 800 g of a.s./ha, preferably 10 to 200 g of a.s./ha.

The combinations with imidazolinones are expediently employed in rice crops which are resistant to the imidazolinones. Such tolerant crops are already known. EP-A-0360750, for example, describes the generation of ALS-inhibitor-tolerant plants by selection methods or genetic engineering methods. The herbicide tolerance of the plants is generated by means of an elevated ALS content in the plants. U.S. Pat. No. 5,198,599 describes sulfonylurea- and imidazolinone-tolerant plants which have been obtained by selection methods.

Examples of PPO inhibitors (A4) are
(A4.1) pyraflufen and its esters, such as pyraflufen-ethyl,
(A4.2) carfentrazone and its esters, such as carfentrazone-ethyl,
(A4.3) oxadiargyl
(A4.4) sulfentrazone
(A4.5) WC9717 or CGA276854=1-allyloxycarbonyl-1-methylethyl2-chloro-5-(3-methyl-2,6-dioxo-4-trifluoromethyl-3,6dihydro-2H-pyrimidin-1-yl)-benzoate (disclosed in U.S. Pat. No. 5,183,492).

The abovementioned azoles are known as inhibitors of the enzyme protoporphyrinogen oxidase (PPO) in plants; see "The Pesticide Manual" 11th Ed., British Crop Protection Council 1997 pp. 1048–1049 for (A4.1), pp. 191–193 for (A4.2), pp. 904–905 for (A4.3) and pp. 1126–1127 for (A4.4). Tolerant crops of plants have already been described. As a rule, the application rates of the azoles are in the range of 1 to 1000 g of a. s./ha, preferably 5 to 200 g of a.s./ha, in particular the following application rates of the individual active substances:
(A4.1) 1 to 20 g of a.s./ha,
(A4.2) 1 to 150 g of a.s./ha, preferably 5–120 g of a.s./ha,
(A4.3) 20 to 500 g of a.s./ha, preferably 50–300 g of a.s./ha,
(A4.4) 50 to 1000 g of a.s./ha, preferably 200–800 g of a.s./ha,
(A4.5) 25 to 500 g of a.s./ha, preferably 250–300 g of a.s./ha.

Some plants which are tolerant to PPO inhibitors are already known.

Possible combination components (B) are, for example, compounds of the subgroups (B0) to (B4) consisting of
(B0) one or more structurally different herbicides from the group (A) mentioned and/or
(B1) foliar-acting and soil-acting herbicides which are effective selectively in rice against monocotyledonous and dicotyledonous harmful plants (residual action) such as, for example,
(B1.1) molinate (PM, pp. 847–849), i.e. S-ethyl azepane-1-thiocarboxylate,
(B1.2) thiobencarb (benthiocarb) (PM, pp. 1192–1193), i.e. S-4-chlorobenzyl diethylthiocarbamate,
(B1.3) quinclorac (PM, pp. 1079–1080), i.e. 3,7-dichloroquinoline-8-carboxylic acid,
(B1.4) propanil (PM, pp. 1017—1019), (=N-(3,4-dichlorophenyl)-propanamide),
(B1.5) pendimethalin (PM, pp. 937–939), i.e. N-(4-ethylpropyl)-2,6-dinitro-3,4-xylidine,
(B1.6) bispyribac, bispyribac-Na (KIH 2023) (PM, pp. 129–131), i.e. sodium 2,6-bis(4,6-dimethoxy-2-pyrimidin-2-yloxy)benzoate,
(B1.7) LGC 40863, i.e. pyribenzoxime (=2,6-bis(4,6-dimethoxy-pyridin-2-yl)-1-[N-(diphenylmethyl)iminooxycarbonyl]benzene, presented at the Brighton Crop Protection Conference Weeds 1997),
(B1.8) butachlor (PM, pp. 159–160), i.e. N-(butoxymethyl)-2-chloro-N-(2,6-diethylphenyl)acetamide,
(B1.9) pretilachlor (PM, pp. 995–996), i.e. 2-chloro-N-(2,6-diethylphenyl)-N-(propoxyethyl)acetamide,
(B1.10) metolachlor (PM, pp. 833–834), i.e. 2-chloro-N-(2-ethyl-6-methylphenyl)-N-(2-methoxy-1-methylethyl)acetamide,
(B1.11) acetochlor (PM, pp. 10–12), i.e. 2-chloro-N-(ethoxymethyl)-N-(2-ethyl-6-methylphenyl)acetamide,
(B1.12) clomazone (PM, pp. 256–257), i.e. 2-(2-chlorobenzyl)-4,4-dimethyl-1,2-oxazolidin-3-one, (B1.13) oxadiargyl (PM, pp. 904–905), i.e. 5-tert-butyl-3-[2,4-dichloro-5-(prop-2-inyloxy)phenyl]-1,3,4-oxadiazol-2(3H)-one, (B1.14) sulfentrazone (PM, pp. 1126–1127), i.e. N-[2,4-dichloro-5-(4-difluoromethyl-4,5-dihydro-3-methyl-5-oxo-1H-1,2,4-triazol-1-yl)phenyl]methanesulfonamide, (B1.15) MY 100, i.e. 3-[1-(3,5-dichlorophenyl)-1,1-dimethyl]-6-methyl-5-phenyl-2H,3H-1,3-oxazin-4-one (Rhone Poulenc), (B1.16) anilofos (PM, pp. 47–48), i.e. S-4-chloro-N-isopropylcarbaniloylmethyl O,O-dimethyl dithiophosphate, (B1.17) cafenstrole (CH 900) (PM, pp. 173–174), (B1.18) mefenacet (PM, pp. 779–781), i.e. 2-(1,3-benzothiazol-2-yloxy)-N-methylacetanilide, (B1.19) fentrazamide (NBA 061), i.e. 4-(2-chlorophenyl)-5-oxo4,5-dihydro-tetrazole-1-carboxylic acid N-cyclohexyl-N-ethylamide, (B1.20) thiazopyr (PM, pp. 1185–1187), i.e. methyl 2-difluoromethyl-5-(4,5-dihydro-1,3-thiazol-2-yl)-4-isobutyl-6-trifluoromethylnicotinate, (B1.21) oxadiazon (PM, pp. 905–907), i.e. 3-tert-butyl-3-(2,4-dichloro-5-isopropoxyphenyl)-1,3,4-oxadiazol-2(3H)-one)

(B1.22) esprocarb (PM, pp. 472–473), i.e. S-benzyl-1,2-dimethylpropyl(ethyl)-thiocarbamate, (B1.23) pyributicarb (PM, pp. 1060–1061), i.e. O-3-tert-butylphenyl 6-(methoxy-2-pyridyl(methyl)thiocarbamate, (B1.24) azimsulfuron (PM, pp. 63–45), i.e. 1-(4,6-dimethoxypyrimidin-2-yl)-3-[1-methyl-4-(2-methyl-2H-tetrazol-5-yl)-pyrazol-5-ylsulfonyl]urea, (B1.25) azoles, such as are disclosed in EP-A-0663913, e.g. 1-(3-chloro-4,5,6,7-tetrahydropyrazolo-[1,5-a]-pyridin-2-yl)-5-methylpropargylamino)-4-pyrazolylcarbonitrile, (B1.26) thenylchlor (PM, pp. 1182–1183), i.e. 2-chloro-N-(2,6-dimethylphenyl)-N[(3-methoxy-2-thienyl) methyllacetamide, (B1.27) pentoxazone (KPP 314) (PM, pp. 942–943), i.e. 3-(4-chloro-5-cyclopentyloxy-2-fluorophenyl)-5-isopropyliden-1,3-oxazolidine-2,4-dione, (B1.28) pyriminobac, pyriminobac-methyl (KIH 6127) (PM, pp. 1071–1072), i.e. 2-(4,6-dimethoxy-2-pyrimidinyloxy)-6-(1-methoxyiminoethyl)benzoic acid), and its salts and esters such as the methyl ester, and/or optionally (B1.29) fluthiamide (fenfenacet, BAY FOE 5043; PM, pp. 82–83) (=N-(4-fluorophenyl)-N-(1-methylethyl)-2-[(trifluoromethyl)-1,3,4-thiadiazol-2-yloxy]acetamide), (B1.30) mesotrione, i.e. 2-(4-mesyl-2-nitrobenzoyl)cyclohexane-1,3-dione (ZA1296, cf. Weed Science Society of America (WSSA) in WSSA Abstracts 1999, Vol. 39, pages 65–66, numbers 130–132), and/or (B1.31) nicosulfuron (PM, pp. 877–879), i.e. 2-(4,6-dimethoxypyrimidin-2-yl)-3-(3-dimethylcarbamoyl-2-pyridylsulfonyl)-urea and its salts, and/or (B2) herbicides which are effective selectively in rice against dicotyledonous harmful plants and/or sedges, for example (B2.1) 2,4-D (PM, pp. 323–327), i.e. (2,4-dichlorophenoxy)acetic acid and its esters and salts, (B2.2) MCPA (PM, pp. 767–769), i.e. (4-chloro-2-methylphenoxy)acetic acid and its esters and salts, (B2.3) bensulfuron-methyl (PM, pp. 104–105), i.e. methyl 2-[[[[[(4,6-dimethoxy-2-pyrimidinyl)amino] carbonyl]-amino]sulfonyl]methyl]benzoate, (B2.4) ethoxysulfuron (PM, pp. 488–489), i.e. 1-(4,6-dimethoxypyrimidin-2-yl)-3(2-ethoxyphenoxysufonyl)urea, (B2.5) metsulfuron and its esters such as the methyl ester (PM, pp. 842–844) (=2-[[[[(4-methoxy-6-methyl-1,3,5-triazin-2-yl)amino]carbonyl]amino]sulfonyl] benzoic acid or its esters such as the methyl ester), (B2.6) acifluorfen (PM, pp. 12–14) and its salts such as the sodium salt (=5-[2-chloro-4-(trifluoromethyl) phenoxy]-2-nitrobenzoic acid or its salts such as the Na salt), (B2.7) cinosulfuron (PM, pp. 248–250), i.e. 1-(4,6-dimethoxy-1,3,5-triazin-2-yl)-3-[2-2-methoxyethoxy)phenylsulfonyl)urea, (B2.8) pyrazosulfuron and its esters such as pyrasulfuron-ethyl (PM, pp. 1052–1054) (=5-(4,6-dimethoxypyrimidin-2-ylcarbamoylsulfamoyl)-1-methylpyrazole-4carboxylic acid or its salts and esters such as the ethyl ester), (B2.9) imazosulfuron (PM, pp. 703–704), i.e. 1-(2-chloroimidazo[1,2-a]pyridin-3-ylsulfonyl)-3-(4,6-dimethoxypyrimidin-2-yl)urea, (B2.10) cyclosulfamuron (PM, pp. 288–289), i.e. 1-(2-(cyclopropyl-carbonyl)phenylsulfamoyl]-3-(4,6-dimethoxypyrimidin-2-yl)urea, (B2.11) chlorsulfuron (PM, pp. 239–240), i.e. 1-(2-chlorophenylsulfonyl)-3-(4-methoxy-6-methyl-1,3,5-triazin-2-yl)urea, (B2.12) bromobutide (PM, pp. 144–145), i.e. 2-bromo-3,3-dimethyl-N-(1-methyl-1-phenylethyl)butyramide, (B2.13) carfentrazone and its esters such as carfentrazone-ethyl (PM, pp. 191–193) (=(RS)-2-chloro-3-[2-chloro-5-(4-difluoromethyl-4,5-dihydro-3-methyl-5-oxo-1H-1,2,4-triazol-1-yl)-4-fluorophenyl] propionic acid and its esters such as the ethyl ester), (B2.14) bentazone (PM, pp. 109–111), i.e. 3-isopropyl-1H-2,1,3-benzothiadiazin-4-(3H)-one-2,2-dioxide), (B2.15) benfuresate (PM, pp. 98–99), i.e. 2,3-dihydro-3,3-dimethylbenzofuran-5-yl ethanesulfonate, (B2.16) chlorimuron and its esters such as chlorimuron-ethyl (PM, pp. 217–218) (=2-(4-chloro-2-methoxypyrimidin-2-ylcarbamoylsulfamoyl)benzoic acid or its esters such as the ethyl ester) and/or optionally (B2.17) dithiopyr (PM, pp. 442–443) (=S,S'-dimethyl 2-difluoromethyl-4-isobutyl-6-trifluoromethylpyridine-3,5-di(thiocarboxylate), (B2.18) tridopyr, i.e. 3,5,6-trichloro-2-pyridyloxyacetic acid, and it salts and esters, and/or (B2.19) tritosulfuron (CAS Reg. No. 142469-14-5; (see AG Chem New Compound Review, Vol. 17, 1999, p. 24, published by AGRANOVA)) (=N-[[[4-methoxy-6-(trifluoromethyl)-1,3,5-triazin-2-yl]amino]carbonyl]-2-(trifluoromethyl)benzenesulfonamide)

and/or (B3) foliar-acting herbicides which are effective selectively in rice against monocotyledonous harmful plants and/or (B3.1) quizalofop-P and its esters such as the ethyl or terfuryl ester (PM, pp. 1089–1092), also in the form of the mixtures of the optical isomers, e.g. the racemic mixture of quizalofop and its esters, (B3.2) fenoxaprop-P and its esters such as the ethyl ester (PM, pp. 519–520), also in the form of the mixtures of the optical isomers, e.g. the racemic mixture of fenoxaprop-ethyl, (B3.3) fluazifop-P and its esters such as the butyl ester (PM, pp. 556–557), also in the form of the mixtures of the optical isomers, e.g. the racemic mixture of fluazifop-butyl, (B3.4) haloxyfop and haloxyfop-P and its esters such as the methyl or the etotyl ester (PM, pp. 660–663) and/or (B3.5) propaquizafop (PM, pp. 1021–1022) and/or optionally (B3.6) clodinafop and its esters such as the propargyl ester (PM, pp. 251–252) (=(R)-2-[4-(5-chloro-3-fluoropyrid-2-yl-oxy)phenoxy]propionic acid or propargyl ester) and/or (B3.7) cyhalofop and its esters such as the butyl ester (PM, pp. 297–298) (=(R)-2-[4-(4-cyano-2-fluorophenoxy)-phenoxy]propionic acid or butyl ester) and/or (B4) foliar- and soil-acting herbicides which are effective selectively in rice against monocotyledonous harmful plants, for example (B4.1) sethoxydim (PM, pp. 1101–1103), (B4.2) cycloxydim (PM, pp. 290–291) and/or (B4.3) clethodim (PM, pp. 250–251) and/or, if appropriate, (B4.4) clefoxidim or "BAS 625 H" (see AG Chem New Compound Review, Vol. 17, 1999, p. 26, published by AGRANOVA) (=2-[1-2-(4-chlorophenoxy)-propoxy-imino)butyl]-3-oxo-5-thion-3-ylcydohex-1-enol).

In the case of active substances based on carboxylic acids or other active substances which form salts or esters, the specification of the herbicides by the common name of the acid is generally also intended to encompass the salts and esters, preferably the commercially available salts and esters, in particular the current commercial form of the active substance.

The application rates of the herbicides (B) may vary greatly from herbicide to herbicide. The following ranges are rules of thumb:

Compounds (B0): 5–2000 g a.s./ha (cf. the information on the group of the compounds (A)), Compounds (B1) 1–7000 g a.s./ha, preferably 10–5000 g a.s./ha, Compounds (B2): 0.1–3000 g a.s./ha, preferably 1–2000 g a.s./ha Compounds (B3): 5–500 g a.s./ha, preferably 10–350 g a.s./ha Compounds (B4): 5–2000 g a.s./ha, preferably 10–1000 g a.s./ha The following specific application rates are preferred (in g of a.s./ha):

(B1.1) 50–5000, preferably 100–4000,
(B1.2) 50–5000, preferably 100–4000,
(B1.3) 30–1200, preferably 40–800,
(B1.4) 50–5000, preferably 100–4000,
(B1.5) 200–5000, preferably 300–3000,
(B1.6) 5–120, preferably 10–90,
(B1.7) 5–120, preferably 10–90,
(B1.8) 100–5000, preferably 200–3000,
(B1.9) 100–5000, preferably 200–3000,
(B1.10) 100–5000, preferably 200–3000,
(B1.11) 100–5000, preferably 200–3000,
(B1.12) 200–1200, preferably 300–1000,
(B1.13) 25–500, preferably 50–300,
(B1.14) 100–1000, preferably 200–800,
(B1.15) 30–150, preferably 40–120,
(B1.16) 50–1500, preferably 75–1200,
(B1.17) 30–3000, preferably 50–1500,
(B1.18) 250–2500, preferably 500–2000,
(B1.19) 50–1000, preferably 100–800,
(B1.20) 50–1000, preferably 100–800,
(B1.21) 50–5000, preferably 100–4000,
(B1.22) 500–5000, preferably 750–4000,
(B1.23) 50–2500, preferably 800–2000,
(B1.24) 10–100, preferably 15–80,
(B1.25) 10–500, preferably 20–300,
(B1.26) 150–500, preferably 200–400,
(B1.27) 100–500, preferably 150–450,
(B1.28) 1060, preferably 15–50,
(B1.29) 200–2000, preferably 250–1500,
(B1.30) 20400, preferably 30–300,
(B1.31) 10–120, preferably 15–90;
(B2.1) 200–2000, preferably 400–1500,
(B2.2) 200–2000, preferably 400–1500,
(B2.3) 5–120, preferably 10–50,
(B2.4) 5–120, preferably 10–50,
(B2.5) 0.1–20, preferably 0.5–10,
(B2.6) 100–500, preferably 120–480,
(B2.7) 15–150, preferably 10–120,
(B2.8) 5–120, preferably 10–60,
(B2.8) 5–120, preferably 10–60,
(B2.9) 5–120, preferably 10–100,
(B2.10) 5–1 00, preferably 10–90,
(B2.11) 1–100, preferably 5–90,
(B2.12) 20–3000, preferably 25–2500,
(B2.13) 1–150, preferably 5–120,
(B2.14) 200–3000, preferably 400–2000,
(B2.15) 50–2000, preferably 100–1500,
(B2.16) 5–120, preferably 10–90,
(B2.17) 30–120, preferably 40–100,
(B2.18) 100–1000, preferably 200–800,
(B2.19) 15–120, preferably 20–100;
(B3.1) 10–150, preferably 20–100,
(B3.2) 10–150, preferably 20–100,
(B3.3) 50–500, preferably 60–400,
(B3.4) 25–400, preferably 30–200,
(B3.5) 5–150, preferably 30–120,
(B3.6) 5–150, preferably 10–120,
(B3.7) 15–450, preferably 25–350;
(B4.1) 100–1500, preferably 150–1200,
(B4.2) 100–1000, preferably 120–900,
(B4.3) 10–400, preferably 20–300,
(B4.4) 50–500, preferably 60–400.

The ratios of compounds (A) and (B) can be deduced from the abovementioned application rates for the individual substances. For example the following ratios are of particular interest:

(A):(B) in the range from 2000:1 to 1:1000, in particular from 200:1 to 1:100, (A):(B0) preferably 400:1 to 1:400, in particular from 200:1 to 1:200, (A1):(B1) preferably 200:1 to 1:250, in particular from 200:1 to 1:100, (A1):(B2) preferably 1500:1 to 1:100, in particular from 200:1 to 1:50, (A1):(B3) preferably 300:1 to 1:30, in particular from 100:1 to 1:10, (A1):(B4) preferably 200:1 to 1:50, in particular from 100:1 to 1:40, very particularly 100:1 to 1:10, (A2):(B1) preferably 200:1 to 1:50, in particular from 100:1 to 1:40, very particularly 100:1 to 1:20,
(A2):(B2) preferably 2000:1 to 1:30, in particular from 1500:1 to 1:20, very particularly 300:1 to 1:10,
(A2):(B3) preferably 400:1 to 1:10, in particular 200:1 to 1:10, very particularly 100:1 to 1:5,
(A2):(B4) preferably 200:1 to 1:20, in particular 100:1 to 1:10,
(A3):(B1) preferably 200:1 to 1:500, in particular 150:1 to 1:500, very particularly 20:1 to 1:500, very particularly from 10:1 to 1:100,
(A3):(B2) preferably 1000:1 to 1:200, in particular 800:1 to 1:200, very particularly 200:1 to 1:200, very particularly 50:1 to 1:50,
(A3):(B3) preferably 1000:1 to 1:1000, in particular, 800:1 to 1:200, very particularly 300:1 to 1:200, very particularly 300:1 to 1:40,
(A3):(B4) preferably 200:1 to 1:1500, in particular 100:1 to 1:1200, very particularly 40:1 to 1:1000,
(A4):(B1) preferably 200:1 to 1:1000, in particular 150:1 to 1:900, very particularly 20:1 to 1:1000, very particularly 10:1 to 1:300,
(A4):(B2) preferably 1000:1 to 1:500, in particular 200:1 to 1:500, very particularly 100:1 to 1:200, very particularly 50:1 to 1:100,
(A4):(B3) preferably 200:1 to 1:100, in particular 150:1 to 1:80, very particularly 20:1 to 1:50, very particularly 10:1 to 1:10,
(A4):(B4) preferably 80:1 to 1:200, in particular 60:1 to 1:200, very particularly 40:1 to 1:200, very particularly 10:1 to 1:50.

The use of the following combinations is of particular interest:
(A1.1)+(B1.1), (A1.1)+(B1.2), (A1.1)+(B1.3), (A1.1)+(B1.4), (A1.1)+(B1.5), (A1.1)+(B1.6), (A1.1)+(B1.7), (A1.1)+(B1.8), (A1.1)+(B1.9), (A1.1)+(B1.10), (A1.1)+(B1.11), (A1.1)+(B1.12), (A1.1)+(B1.13), (A1.1)+(B1.14), (A1.1)+(B1.15), (A1.1)+(B1.16), (A1.1)+(B1.17), (A1.1)+(B1.18), (A1.1)+(B1.19), (A1.1)+(B1.20), (A1.1)+(B1.21), (A1.1)+(B1.22), (A1.1)+(B1.23), (A1.1)+(B1.24), (A1.1)+(B1.25), (A1.1)+(B1.26), (A1.1)+(B1.27), (A1.1)+(B1.28), (A1.1)+(B1.29), (A1.1)+(B1.30), (A1.1)+(B1.31), (A1.2)+(B1.1), (A1.2)+(B1.2), (A1.2)+(B1.3), (A1.2)+(B1.4), (A1.2)+(B1.5), (A1.2)+(B1.6), (A1.2)+(B1.7), (A1.2)+(B1.8), (A1.2)+(B1.9), (A1.2)+(B1.10), (A1.2)+(B1.11), (A1.2)+(B1.12), (A1.2)+(B1.13), (A1.2)+(B1.14), (A1.2)+(B1.15), (A1.2)+(B1.16), (A1.2)+(B1.17), (A1.2)+(B1.18), (A1.2)+(B1.19), (A1.2)+(B1.20), (A1.2)+(B1.21), (A1.2)+(B1.22), (A1.2)+(B1.23), (A1.2)+(B1.24), (A1.2)+(B1.25), (A1.2)+(B1.26), (A1.2)+(B1.27), (A1.2)+(B1.28), (A1.2)+(B1.29), (A1.2)+(B1.30), (A1.2)+(B1.31), (A1.1)+(B2.1), (A1.1)+(B2.2), (A1.1)+(B2.3), (A11)+(B2.4), (A1.1)+(B2.5), (A1.1)+(B2.6), (A1.1)+(B2.7), (A1.1)+(B2.8), (A1.1)+(B2.9), (A1.1)+(B2.10), (A1.1)+(B2.11), (A1.1)+(B2.12), (A1.1)+(B2.13), (A1.1)+(B2.14), (A1.1)+(B2.15), (A1.1)+(B2.16), (A1.1)+(B2.17), (A1.1)+(B2.18), (A1.1)+(B2.19), (A1.2)+(B2.1), (A1.2)+(B2.2), (A1.2)+(B2.3), (A1.2)+(B2.4), (A1.2)+(B2.5), (A1.2)+(B2.6), (A1.2)+(B2.7), (A1.2)+(B2.8), (A1.2)+(B2.9), (A1.2)+(B2.10), (A1.2)+(B2.11), (A1.2)+(B2.12), (A1.2)+(B2.13), (A1.2)+(B2.14), (A1.2)+(B2.15), (A1.2)+(B2.16), (A1.2)+(B2.17), (A1.2)+(B2.18), (A1.2)+(B2.19), (A1.1)+(B3.1), (A1.1)+(B3.2), (A1.1)+(B3.3), (A1.1)+(B3.4), (A1.1)+(B3.5), (A1.1)+(B3.6), (A1.1)+(B3.7), (A1.2)+(B3.1), (A1.2)+(B3.2), (A1.2)+(B3.3), (A1.2)+(B3.4), (A1.2)+(B3.5), (A1.2)+(B3.6), (A1.2)+(B3.7), (A1.1)+(B4.1), (A1.1)+(B4.2), (A1.1)+(B4.3), (A1.1)+(B4.4), (A1.2)+(B4.1), (A1.2)+(B4.2), (A1.2)+(B4.3), (A1.2)+(B4.4),
(A2.2)+(B1.1), (A2.2)+(B1.2), (A2.2)+(B1.3), (A2.2)+(B1.4), (A2.2)+(B1.5), (A2.2)+(B1.6), (A2.2)+(B1.7), (A2.2)+(B1.8), (A2.2)+(B1.9), (A2.2)+(B1.10), (A2.2)+(B1.11), (A2.2)+(B1.12), (A2.2)+(B1.13), (A2.2)+(B1.14), (A2.2)+(B1.15), (A2.2)+(B1.16), (A2.2)+(B1.17), (A2.2)+(B1.18), (A2.2)+(B1.19), (A2.2)+(B1.20), (A2.2)+(B1.21), (A2.2)+(B1.22), (A2.2)+(B1.23), (A2.2)+(B1.24), (A2.2)+(B1.25), (A2.2)+(B1.26), (A2.2)+(B1.27), (A2.2)+(B1.28), (A2.2)+(B1.29), (A2.2)+(B1.30), (A2.2)+(B1.31), (A2.2)+(B2.1), (A2.2)+(B2.2), (A2.2)+(B2.3), (A2.2)+(B2.4), (A2.2)+(B2.5), (A2.2)+(B2.6), (A2.2)+(B2.7), (A2.2)+(B2.8), (A2.2)+(B2.9), (A2.2)+(B2.10), (A2.2)+(B2.11), (A2.2)+(B2.12), (A2.2)+(B2.13), (A2.2)+(B2.14), (A2.2)+(B2.15), (A2.2)+(B2.16), (A2.2)+(B2.17), (A2.2)+(B2.18), (A2.2)+(B2.19), (A2.2)+(B3.1), (A2.2)+(B3.2), (A2.2)+(B3.3), (A2.2)+(B3.4), (A2.2)+(B3.5), (A2.2)+(B3.5), (A2.2)+(B3.6), (A2.2)+(B3.7), (A2.2)+(B4.1), (A2.2)+(B4.2), (A2.2)+(B4.3), (A2.2)+(B4.4), In the case of the combination of a compound (A) with one or more compounds (B0), this is, according to the definition, a combination of two or more compounds from group (A). Because of the broad-spectrum herbicides (A), the condition for such a combination is that the transgenic plants or mutants show cross-resistance to various herbicides (A). Such cross-resistances in transgenic plants have already been disclosed; cf. WO-A-98/20144.

In individual cases, it may be meaningful to combine one or more of the compounds (A) with more than one compound (B), preferably from amongst classes (B1), (B2), (B3) and (B4).

Moreover, the combinations according to the invention can be employed together with other active substances, for example from the group of the safeners, fungicides, insecticides and plant growth regulators, or from the group of the additives and formulation auxiliaries conventionally used in crop protection. Additives are, for example, fertilizers and colors.

Preferred are herbicide combinations of one or more compounds (A) with one or more compounds from the group (B1) or (B2) or (B3) or (B4).

Also preferred are combinations of one or more compounds (A), for example (A1.2)+(A2.2), preferably of a compound (A), with one or more compounds (B) as shown in the scheme:
(A)+(B1)+(B2), (A)+(B1)+(B3), (A)+(B1)+(B4), (A)+(B2)+(B3), (A)+(B1)+(B2)+(C), (A)+(B1)+(B3)+(C), (A)+(B1)+(B4)+(C), (A)+(B2)+(B4)+(C), oder (A)+(B3)+(B4)+(C).

Combinations to which one or more other active substances of a different structure [active substances (C)], if appropriate safeners, are added are also according to the invention, for example
(A)+(B1)+(C), (A)+(B2)+(C), (A)+(B3)+(C), or (A)+(B4)+(C), (A)+(B1)+(B2)+(C), (A)+(B1)+(B3)+(C), (A)+(B1)+(B4)+(C), (A)+(B2)+(B4)+(C) or (A)+(B3)+(B4)+(C).

The preferred conditions illustrated hereinbelow also apply to combinations of the last-mentioned type with three or more active substances, in particular to two-way-combinations according to the invention, mainly when they contain the two-way-combinations according to the invention.

Also of particular interest is the use according to the invention of the combinations with one or more herbicides from the group (A), preferably (A1.2) or (A2.2), in particular (A1.2), and with one or more herbicides, preferably one herbicide, from the group which consists of:
- (B0') one or more structurally different herbicides from the abovementioned group (A) and/or
- (B1') foliar-acting and soil-acting herbicides which are effective selectively in rice against monocotyledonous and dicotyledonous harmful plants (residual action) such as molinate, thiobencarb, quindorac, propanil, pendimethalin, bispyribac-Na, LGC 40863, butachlor, pretilachlor, acetochlor, clomazone, oxadiargyl, sulfentrazone, MY 100, anilofos, cafenstrole (CH 900), mefenacet, fentrazamid, thiazopyr, oxadiazon and/or pyriminobac-methyl (KIH 6127) and/or optionally fluthiamide and/or mesotrione and/or
- (B2') herbicides which are effective selectively in rice against dicotyledonous harmful plants and/or sedges, for example bensulfuron-methyl, ethoxy-sulfuron, acifluorfen, pyrazosulfuron, imazosulfuron, cyclosulfamuron, chlorsulfuron, bromobutide, carfentrazone, bentazone, benfuresate and/or chlorimuron and/or, if appropriate, trisulfuron and/or
- (B3') foliar-acting herbicides which are effective selectively in rice against monocotyledonous harmful plants, for example quizalofop-P, fenoxaprop-P, fluazifop-P, haloxyfop and/or haloxyfop-P and/or optionally clodinafop and/or cyhalofop and/or
- (B4') foliar- and soil-acting herbicides which are effective selectively in rice against monocotyledonous harmful plants, such as sethoxydim, cycloxydim and/or clethodim and/or, if appropriate, clefoxidim or of herbicides from a number of the groups (B0') to (B4').

In this case, the combinations of the respective component (A) with one or more herbicides from the group (B1'), (B2'), (B3') or (B4') are preferred. The combinations (A)+(B1')+(B2'), (A)+(B1')+(B3'), (A)+(B1')+(B4'), (A)+(B2')+(B3'), (A)+(B2')+(B4') or (A)+(B3')+(B4') are also preferred.

Some of the herbicide combinations which are to be used according to the invention are novel, preferably those of the combinations (A)+(B').

The combinations according to the invention (=herbicidal compositions) have an outstanding herbicidal activity against a broad spectrum of economically important monocotyledonous and dicotyledonous harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Post-emergence application, or early post-sowing pre-emergence application, is preferred.

Specifically, examples may be mentioned of some representatives of the monocotyledonous and dicotyledonous weed flora which can be controlled by the compounds according to the invention, without the enumeration being a restriction to certain species.

Examples of weed species on which the herbicidal compositions act efficiently are, from amongst the monocots, *Echinochloa* spp., *Brachiaria* spp., *Leptochloa* spp. and *Digitaria* spp., but also *Panicum* spp., *Agropyron* spp., wild cereal forms and *Sorghum* spp., *Setaria* spp., *Alopecurus* spp., *Avena* spp., *Apera spica venti*, *Lolium* spp., *Phalaris* spp., *Cynodon* spp., *Poa* spp., and *Cyperus* species and *Imperata*.

In the case of the *dicotyledonous* weed species, the spectrum of action extends to species such as, for example, *Amaranthus* spp., *Sphenoclea* spp., *Heteranthera* spp., *Eleocharis* spp., *Ipomoea* spp., *Eschynomena* spp., *Sesbania* spp. und *Cyperrus* spp. gut erfaßt, aber auch *Polygonum* spp., *Xanthium* spp., *Equisetum*, *Chenopodium* spp., *Abutilon* spp., *Anthemis* spp., *Lamium* spp., *Matricaria* spp., *Stellaria* spp., *Kochia* spp., *Viola* spp., *Datura* spp., *Chrysanthemum* spp., *Thiaspi* spp., *Pharbitis* spp., *Sida* spp., *Sinapis* spp., *Cupsella* spp., *Ambrosia* spp., *Galium* spp., *Emex* spp., *Lamium* spp., *Papaver* spp., *Solanum* spp., *Cirsium* spp., *Veronica* spp. *Convolvulus* spp., *Rumex* and *Artemisia*.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

In comparison with the individual preparations, the herbicidal compositions according to the invention are distinguished by a more rapidly commencing and longer lasting herbicidal action. As a rule, the rainfastness of the active substances in the combinations according to the invention is advantageous. A particular advantage is that the dosages of the compounds (A) and (B), which are used in the combinations and are effective, can be adjusted to such a low quantity that their soil action is optimal. This does not only allow them to be employed in sensitive crops in the first place, but groundwater contaminations are virtually avoided. The active-substance-combination according to the invention allows the application rate of the active substances required to be reduced considerably.

When herbicides of the type (A)+(B) are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and grass weeds to be controlled, the herbicidal effect to take place more rapidly, the duration of action to be longer, the harmful plants to be controlled better while using only one, or few, applications, and the application period which is possible to be extended. In some cases, uptake of the compositions also reduces the amount of harmful constituents in the crop plant, such as nitrogen or oleic acid. The abovementioned properties and advantages are necessary under practical weed control conditions to keep agricultural crops free from undesired competing plants and thus to guarantee and/or increase the yields from the qualitative and quantitative point of view. These novel combinations markedly exceed the technical state of the art with a view to the properties described.

While the compounds according to the invention have an outstanding herbicidal activity against monocotyledonous and dicotyledonous weeds, the tolerant, or cross-tolerant, rice plants are damaged only to a minor extent, or not at all.

Moreover, some of the compositions according to the invention have outstanding growth-regulatory properties on the rice plants. They engage in the plants' metabolism in a regulatory manner and can thus be employed for provoking directed effects on plant constituents. Moreover, they are also suitable for the general control and inhibition of undesired vegetative growth without simultaneously destroying the plants. An inhibition of vegetative growth is very important in a large number of monocotyledonous and dicotyledonous crops since lodging can thus be reduced, or prevented completely.

Owing to their herbicidal and plant-growth-regulatory properties, the compositions can be employed for controlling harmful plants in known tolerant or cross-tolerant rice crops, or in tolerant or genetically engineered rice crops still to be developed. As a rule, the transgenic plants are distinguished by particular, advantageous properties, in addition to resistances to the compositions according to the invention, for example, by resistances to plant diseases or pathogens of plant diseases such as particular insects or microorganisms such as fungi, bacteria or viruses. Other particular properties relate, for example, to the harvested material with regard to quantity, quality, storability, composition and specific constituents. Thus, transgenic plants are known whose oil content is increased or whose quality is altered, for example where the harvested material has a different fatty acid composition.

Conventional methods of generating novel plants which have modified properties in comparison to plants occurring to date consist, for example, in traditional breeding methods and the generation of mutants. Alternatively, novel plants with altered properties can be generated with the aid of genetic engineering methods (see, for example, EP-A0221044, EP-A-0131624). For example, the following were described in several cases:

the modification, by genetic engineering, of crop plants with the aim of modifying the starch synthesized in the plant (for example WO 92/11376, WO 92/14827, WO 91/19806), transgenic crop plants which exhibit resistances to other herbicides, for example to sulfonylureas (EP-A0257993, U.S. Pat. No. 5,013,659), transgenic crop plants with the capability of producing *Bacillus thuringiensis* toxins (Bt toxins), which make the plants resistant to certain pests (EP-A-0142924, EP-A0193259), transgenic crop plants with a modified fatty acid composition (WO 91/13972).

A large number of techniques in molecular biology with the aid of which novel transgenic plants with modified properties can be generated are known in principle; see, for example, Sambrook et al., 1989, Molecular Cloning, A Laboratory Manual, 2nd Edition, Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423–431.

To carry out such genetic engineering manipulations, nucleic acid molecules which allow mutagenesis or sequence changes by recombination of DNA sequences can be introduced in plasmids. For example, the abovementioned standard methods allow base changes to be carried out, subsequences to be removed, or natural or synthetic sequences to be added. To connect the DNA fragments to each other, adaptors or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use, on the one hand, DNA molecules which encompass the entire encoding sequence of a gene product inclusive of any flanking sequences which may be present, as well as DNA molecules which only encompass portions of the encoding sequence, it being necessary for these portions to be long enough to have an antisense effect on the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the encoding region with DNA sequences which ensure localization in a particular compartment. Such sequences are known to those skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give rise to whole plants. In principle, the transgenic plants can be plants of any desired plant species, i.e. not only *monocotyledonous*, but also *dicotyledonous*, plants.

Thus, transgenic plants can be obtained whose properties are altered by overexpression, suppression or inhibition of homologous (=natural) genes or gene sequences or the expression of heterologous (=foreign) genes or gene sequences.

The invention therefore also relates to a method of controlling undesired vegetation in tolerant rice crops, which comprises applying one or more herbicides of the type (A) and one or more herbicides of the type (B) to the harmful plants, parts of these plants, or the area under cultivation.

The invention also relates to the novel combinations of compounds (A)+(B) and to herbicidal compositions comprising them.

The active substance combinations according to the invention can exist not only as formulation mixes of the two components, if appropriate together with other active substances, additives and/or conventional formulation auxiliaries, which are then applied in the customary manner after dilution with water, but also as so-called tank mixes by jointly diluting the separately formulated, or partially separately formulated, components with water.

Compounds (A) and (B) or their combinations can be formulated in different ways, depending on the biological and/or chemico-physical parameters which prevail. The following are examples of general possibilities for formulations: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed-dressing materials, granules for soil application or for broadcasting, or water dispersible granules (WG), ULV formulations, microcapsules or waxes.

The individual formulation types are known in principle and are described, for example, in: Winnacker-Kuchler "Chemische Technologie" Chemical engineering], Volume 7, C. Hauser Verlag Munich, 4th Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4th Edition 1986.

Based on these formulations, combinations with other pesticidally active substances, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active substance, also comprise ionic or non-ionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutyinaphthalenesulfonate or else sodium oleoylmethyltauride, in addition to a diluent or inert material.

Emulsifiable concentrates are prepared by dissolving the active substance in an organic solvent, for example butanol, cyclohexanone, dimethylformamide, xylene or else higher-boiling aromatic or hydrocarbons with addition of one or more ionic or non-ionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active substance with finely divided solid materials, for example talc, natural clays such as kaolin, bentonite and pyrophyllite, or diatomateous earth.

Granules can be prepared either by spraying the active substance onto adsorptive, granulated inert material or by applying active substance concentrates to the surface of carriers such as sand, kaolites or granulated inert material with the aid of binders, for example polyvinyl alcohol, sodium polyacrylate or else mineral oils. Suitable active substances may also be granulated in the manner conventionally used for the production of fertilizer granules, if desired in a mixture with fertilizers. As a rule, water-dispersible granules are prepared by processes such as spray drying, fluidized-bed granulation, disk granulation, mixing with high-speed mixers and extrusion without solid inert material.

As a rule, the agrochemical preparations comprise 0.1 to 99 percent by weight, in particular 2 to 95% by weight, of active substances of the types A and/or B, the following concentrations being customary, depending on the type of formulation: The active substance concentration in wettable powders is, for example, approximately 10 to 95% by weight, the remainder to 100% by weight being composed of customary formulation constituents. In the case of emulsifiable concentrates, the active substance concentration may amount to, for example, 5 to 80% by weight.

Formulations in the form of dusts comprise, in most cases, 5 to 20% by weight of active substance, sprayable solutions approximately 0.2 to 25% by weight of active substance.

In the case of granules such as dispersible granules, the active substance content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active substance formulations may comprise, if appropriate, the conventional adhesives, wetters, dispersants, emulsifiers, preservatives, antifreeze agents, solvents, fillers, colors, carriers, antifoams, evaporation inhibitors, pH regulators or viscosity regulators.

For example, it is known that the effect of glufosinate-ammonium (A1.2) and of its L-enantiomer can be improved by surfactants, preferably by wetters from the series of the alkyl polyglycol ether sulfates which contain, for example, 10 to 18 carbon atoms and which are used in the form of their alkali metal salts or ammonium salts, but also as the magnesium salt, such as sodium $C_{12}/C_{14}$-fatty alcohol diglycol ether sulfate (®Genapol LRO, Hoechst); see EP-A-0476555, EP-A0048436, EP-A0336151 or U.S. Pat. No. 4,400,196 and Proc. EWRS Symp. "Factors Affecting Herbicidal Activity and Selectivity", 227–232 (1988). Moreover, it is known that alkyl polyglycol ether sulfates are also suitable as penetrants and synergists for a series of other herbicides, inter alia also herbicides from the series of the imidazolinones; see EP-A-0502014.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further prior to use with other inert substances.

The active substances can be applied to the plants, parts of the plants, seeds of the plants or the area under cultivation (soil of a field), preferably to the green plants and parts of the plants and, if appropriate, additionally to the soil of the field.

One possible use is the joint application of the active substances in the form of tank mixes, the concentrated formulations of the individual active substances, in optimal formulations, jointly being mixed with water in the tank and the resulting spray mixture being applied.

A joint herbicidal formulation of the combination according to the invention of the active substances (A) and (B) has the advantage of being easier to apply since the quantities of the components are already presented in the correct ratio to each other Moreover, the adjuvants in the formulation can be matched optimally to each other, while a tank mix of different formulations may lead to undesired combinations of adjuvants.

A. General Formulation Examples
- a) A dust is obtained by mixing 10 parts by weight of an active substance/active substance mixture and 90 parts by weight of talc as inert material and comminuting the mixture in a hammer mill.
- b) A wettable powder which is readily dispersible in water is obtained by mixing 25 parts by weight of an active substance/active substance mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.
- c) A dispersion concentrate which is readily dispersible in water is obtained by mixing 20 parts by weight of an active substance/active substance mixture with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to 277°C.), and grinding the mixture in a ball mill to a fineness of below 5 microns.

d) An emulsifiable concentrate is obtained from 15 parts by weight of an active substance/active substance mixture, 75 parts by weight of cyclohexanone as solvent and 10 parts by weight of oxethylated nonylphenol as emulsifier.
e) Water-dispersible granules are obtained by mixing 75 parts by weight of an active substance/active substance mixture, 10 parts by weight of calcium lignosulfonate, 5 parts by weight of sodium lauryl sulfate, 3 parts by weight of polyvinyl alcohol and 7 parts by weight of kaolin, grinding the mixture on a pinned-disk mill and granulating the powder in a fluidized bed by spraying on water as granulation liquid.
f) Water-dispersible granules are also obtained by homogenizing and precomminuting, on a colloid mill, 25 parts by weight of an active substance/active substance mixture, 5 parts by weight of sodium 2,2'-dinaphthyl-methane-6,6'-disulfonate, 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance model.

Biological Examples

1. Pre-Emergence Effect on Weeds

Seeds or rhizome pieces of monocotyledonous and dicotyledonous weed plants are placed in sandy loam soil in plastic pots and covered with soil. The compositions which are formulated in the form of concentrated aqueous solutions, wettable powders or emulsion concentrates are then applied to the surface of the soil cover in the form of an aqueous solution, suspension or emulsion at an application rate of 600 to 800 l of water/ha (converted), in various dosages. After the treatment, the pots are placed in a greenhouse and kept under good growth conditions for the weeds. After the test plants have emerged, the damage to the plants or the negative effect on the emergence is scored visually after a test period of 3 to 4 weeks by comparison with untreated controls. As shown by the test results, the compositions according to the invention have a good herbicidal preemergence activity against a broad spectrum of grass weeds and dicotyledonous weeds.

Frequently, effects of the combinations according to the invention are observed which exceed the formal total of the effects when applying the herbicides individually (=synergistic effect).

If the data of the effects observed already exceed the formal total ($=E^A$) of the data of the experiments with individual applications, then they also exceed Colby's expected value ($=E^C$), which is calculated by the formula which follows and which is also considered to be suggestive of synergism (cf. S. R. Colby; in Weeds 15 (1967) pp. 20 to 22):

$$E = A + B - (A \cdot B/100)$$

A, B denote the effect of the active substances A, or in %, for a or b g of a.s./ha; E denotes the expected value in % for a+b g a.s./ha.

At suitable low dosages, the observed data of the experiments show an effect of the combinations above Colby's expected values.

2. Post-Emergence Effect on Weeds

Seeds or rhizome pieces of monocotyledonous and dicotyledonous weeds are placed in sandy loam soil in cardboard pots, covered with soil and grown in the greenhouse under good growth conditions. Three weeks after sowing, the test plants in the three-leaf stage are treated with the compositions according to the invention. The compositions according to the invention which are formulated as wettable powders or as emulsion concentrates are sprayed in various dosages on the green parts of the plants at an application rate of 600 to 800 l of water/ha (converted). After the test plants have remained in the greenhouse for about 3 to 4 weeks under optimal growth conditions, the effect of the products is scored visually by comparison with untreated controls. When applied post-emergence, too, the compositions according to the invention have a good herbicidal activity against a broad spectrum of economically important grass weeds and broad-leaved weeds.

Frequently, effects of the combinations according to the invention are observed which exceed the formal total of the effects when applying the herbicides individually. At suitable low dosages, the observed data of the experiments show an effect of the combinations above Colby's expected values. (cf. score figures in Example 1).

3. Effect on Harmful Plants in Rice (Paddy Rice)

Transplanted and sown rice as well as typical rice weeds and weed grasses are raised in closed plastic pots in a greenhouse up to the three-leaf stage (*Echinochloa crus-galli* 1.5 leaf) under paddy rice conditions (flooding height of the water: 2–3 cm). The treatment with the compounds according to the invention is then carried out. For this: the formulated active substances are suspended, dissolved or emulsified in water and poured into the flooding water of the test plants in different dosages. After the treatment carried out in this way, the test plants are placed in the greenhouse under optimal growth conditions and kept in this way during the entire test period. Approximately three weeks after the application, evaluation is carried out by means of optical assessment of the plant damage in comparison with untreated controls. The combinations according to the invention have a very good herbicidal action against harmful plants which are typical of rice crops.

4. Herbicidal Effect and Tolerance by Crop Plants (Field Trial)

Transgenic rice plants with a resistance to one or more herbicides (A) together with typical weed plants were grown in the open on 2×5 m plots under natural field conditions; alternatively, weed infestation occurred naturally when the rice plants were grown. Fields were set up for field rice or alternatively also for paddy rice. The treatment with the compositions according to the invention and, as control, separately by only applying the active substances of the components, was carried out under standard conditions, e.g. with a plot sprayer at an application rate of 200–300 liters of water per hectare in parallel tests as can be seen from the scheme in Table 1 (no pre-sowing treatment with paddy rice):

TABLE 1

| | Use scheme - examples | | | | |
|---|---|---|---|---|---|
| Application of the active substances | Pre-sowing | Pre-emergence post-sowing | Post-emergence 1-2-leaf | Post-emergence 2-4-leaf | Post-emergence 6-leaf |
| combination | (A) + (B) | | | | |
| " | | (A) + (B) | | | |
| " | | | (A) + (B) | | |
| " | | | | (A) + (B) | |
| " | | | | | (A) + (B) |
| sequential | (A) + (B) | (A) + (B) | | | |
| " | | (A) + (B) | (A) + (B) | | |
| " | | (B) | | (A) | |
| " | | (B) | | (A) + (B) | |
| " | | | (A) + (B) | (A) + (B) | |

TABLE 1-continued

Use scheme - examples

| Application of the active substances | Pre-sowing | Pre-emergence post-sowing | Post-emergence 1-2-leaf | Post-emergence 2-4-leaf | Post-emergence 6-leaf |
|---|---|---|---|---|---|
| " | | | (A) + (B) | (A) + (B) | (A) + (B) |
| " | (B) | | (A) | (A) + (B) | |
| " | | (B) | | (A) + (B) | (A) + (B) |
| " | | | | (A) + (B) | (A) + (B) |
| " | | | (A) | (A) + (B) | (A) + (B) |

2, 4, 6 and 8 weeks after the application, the herbicidal activity of the active substances or active substance mixtures was scored visually with reference to the treated plots in comparison to untreated control plots. The damage to, and the development of, all aerial parts of the plants was recorded. Scoring was done on the basis of a percentage sale (100% action=all plants destroyed; 50% action=50% of the plants and green parts of the plants destroyed; 0% action=no recognizable effect=like control plot. The mean of the score values of in each case 4 plots was calculated.

The comparison demonstrated that the herbicidal effect of the combinations according to the invention was usually higher, in some cases considerably higher, than the total of the effects of the individual herbicides. In essential periods of the period of scoring, the effects were greater than Colby's expected values (cf. scoring in Example 1) and therefore suggest a synergism. In contrast, the rice plants were not damaged owing to the treatments with the herbicidal compositions, or were only damaged to a negligible extent.

Abbreviations generally used in the following tables:

g of a.s./ha=gram of active substance (100% active substance) per hectare $E^A$=Total of the herbicidal effects of the individual applications $E^C$=Colby's expected value (cf. scoring in Table 1)

TABLE 2

Herbicidal effect in rice broad-leaved weeds

| Active substance(s) | Dose[1] g A.S./ha | Herbicidal action[2] (%) against Echinochloa crus-galli |
|---|---|---|
| (A1.2) | 400 | 93 |
| (B2.3) | 45 | 0 |
| (A1.2) + (B2.3) | 400 + 45 | 99 |

Abbreviations for Table 2:
[1]= Application in the 3–4-leaf stage
[2]= Scoring 2 weeks after application
(A1.2) = glufosinate-ammonium
(B2.3) = bensulfuron-methyl

TABLE 3

Herbicidal effect in rice weeds

| Active substance(s) | Dose[1] g A.S./ha | Herbicidal action[2] (%) against Ipomoea sp. |
|---|---|---|
| (A1.2) | 400 | 93 |
| (B1.4) | 3360 | 90 |
| (A1.2) + (B1.4) | 400 + 3360 | 100 ($E^C$ = 99.8) |

Abbreviations for Table 3:
[1]= Application in the 4-leaf stage
[2]= Scoring 2 weeks after application
(A1.2) = glufosinate-ammonium
(B1.4) = propanil

TABLE 4

Herbicidal effect in rice weeds (field trial)

| Active substance(s) | Dose[1] g A.S./ha | Herbicidal action[2] (%) against Echinochloa crus-galli |
|---|---|---|
| (A1.2) | 250 | 63 |
| | 500 | 87 |
| (B1.12) | 400 | 7 |
| (A1.2) + (B1.12) | 250 + 400 | 70 ($E^C$ = 65.6) |
| | 500 + 400 | 96 ($E^A$ = 94) |

Abbreviations for Table 4:
[1]= Application in the 4-leaf stage
[2]= Scoring 42 days after application
(A1.2) = glufosinate-ammonium
(B1.12) = clomazone

TABLE 5

Herbicidal effect in rice weeds (field trial)

| Active substance(s) | Dose[1] g A.S./ha | Herbicidal action[2] (%) against Cyperus difformis |
|---|---|---|
| (A1.2) | 500 | 40 |
| | 400 | 18 |
| (B2.3) | 70 | 87 |
| | 35 | 55 |
| (A1.2) + (B2.3) | 400 + 37 | 97 ($E^A$ = 73) |
| (B2.13) | 50 | 28 |
| (A1.2) + (B2.13) | 400 + 50 | 88 ($E^A$ = 46) |
| (B2.8) | 15 | 65 |
| (A1.2) + (B2.8) | 400 + 15 | 92 ($E^A$ = 83) |
| (B2.15) | 200 | 35 |
| (A1.2) + (B2.15) | 400 + 200 | 65 ($E^A$ = 53) |

Abbreviations for Table 5:
[1]= Application in the 3-leaf stage
[2]= Scoring 36 days after application
(A1.2) = glufosinate-ammonium
(B2.3) = bensulfuron-methyl
(B2.13) = carfentrazone-ethyl
(B2.8) = pyrazosulfuron-ethyl
(B2.15) = benfuresate

TABLE 6

Herbicidal effect in rice weeds (field trial)

| Active substance(s) | Dose[1] g A.S./ha | Herbicidal action[2] (%) against Cyperus iria |
|---|---|---|
| (A1.2) | 400 | 35 |
| (B1.21) | 250 | 37 |
| (A1.2) + (B1.21) | 400 + 250 | 85 ($E^A$ = 72) |
| (B1.5) | 1000 | 33 |
| (A1.2) + (B1.5) | 400 + 1000 | 78 ($E^A$ = 92) |
| (B1.2) | 1500 | 57 |
| (A1.2) + (B1.2) | 400 + 1500 | 96 ($E^A$ = 92) |
| (B2.5) | 1 | 35 |
| (A1.2) + (B2.5) | 400 + 1 | 83 ($E^A$ = 70) |
| (B2.1) | 500 | 62 |
| (A1.2) + (B2.1) | 400 + 500 | 99 ($E^A$ = 97) |

Abbreviations for Table 6:
[1]= Application in the 3-leaf stage
[2]= Scoring 42 days after application
(A1.2) = glufosinate-ammonium
(B1.21) = oxadiazon
(B1.5) = pendimethalin
(B1.2) = thiobencarb
(B2.5) = metsulfuron-methyl
(B2.1) = 2,4-D

TABLE 7

Herbicidal effect in rice weeds (field trial)

| Active substance(s) | Dose[1] g A.S./ha | Herbicidal action[2] (%) against *Echinochloa crus galli* |
|---|---|---|
| (A1.2) | 400 | 65 |
| (B1.3) | 560 | 25 |
| (A1.2) + (B1.3) | 400 + 560 | 93 ($E^A = 90$) |
| (B3.2) | 45 | 15 |
| (A1.2) + (B3.2) | 400 + 45 | 88 ($E^A = 80$) |

Abbreviations for Table 7:
[1]= Application in the 3-leaf stage
[2]= Scoring 42 days after application
(A1.2) = glufosinate-ammonium
(B1.3) = quinclorac
(B3.2) = fenoxaprop-ethyl

TABLE 8

Herbicidal effect in rice weeds (field trial)

| Active substance(s) | Dose[1] g A.S./ha | Herbicidal action[2] (%) against *Aeschynomene rudis* |
|---|---|---|
| (A1.2) | 500 | 83 |
|  | 250 | 65 |
| (B1.16) | 450 | 27 |
| (A1.2) + (B1.16) | 400 + 450 | 96 ($E^A = 92$) |

Abbreviations for Table 8:
[1]= Application in the 3-leaf stage
[2]= Scoring 28 days after application
(A1.2) = glufosinate-ammonium
(B1.16) = anilofos

TABLE 9

Herbicidal effect in rice weeds (field trial)

| Active substance(s) | Dose[1] g A.S./ha | Herbicidal action[2] (%) against *Echinochloa crus galli* |
|---|---|---|
| (A1.2) | 500 | 18 |
| (B1.1) | 4480 | 0 |
| (A1.2) + (B1.1) | 500 + 4480 | 70 ($E^A = 18$) |
| (A3.2) | 75 | 67 |
| (A1.2) + (A3.2) | 500 + 75 | 95 ($E^A = 86$) |

Abbreviations for Table 9:
[1]= Application in the 5-6-leaf stage
[2]= Scoring 36 days after application
(A1.2) = glufosinate-ammonium
(B1.1) = molinate
(A3.2) = imazethapyr

TABLE 10

Herbicidal effect in rice weeds (field trial)

| Active substance(s) | Dose[1] g A.S./ha | Herbicidal action[2] (%) against *Cyperus difformis* |
|---|---|---|
| (A2.2) | 840 | 38 |
| (B2.4) | 15 | 40 |
| (A2.2) + (B2.4) | 840 + 15 | 95 ($E^A = 78$) |

Abbreviations for Table 10:
[1]= Application in the 7-leaf stage
[2]= Scoring 36 days after application
(A2.2) = glyphosate-isopropylammonium
(B2.4) = ethoxysulfuron

TABLE 11

Herbicidal effect in rice weeds (field trial)

| Active substance(s) | Dose[1] g A.S./ha | Herbicidal action[2] (%) against *Echinochloa crus-galli* |
|---|---|---|
| (A1.2) | 500 | 75 |
|  | 250 | 35 |
| (B4.4) | 75 | 83 |
|  | 37.5 | 50 |
| (A1.2) + (B4.4) | 250 + 37.5 | 93 ($E^A = 85$) |

Abbreviations for Table 11:
[1]= Application in the 4-leaf stage
[2]= Scoring 26 days after application
(A2.2) = glufosinate-ammonium
(B4.4) = clefoxidim

The invention claimed is:

1. A herbicidal composition which comprises the combination of:
   (A) glufosinate or salts thereof; and
   (B) one or more herbicides selected from the group of compounds consisting of
      (B1) foliar- and soil-acting herbicides which are effective selectively in rice against monocotyledonous and dicotyledonous harmful plants selected from the group consisting of molinate, anilofos, and oxadiazon; and
      (B2) herbicides which are effective selectively in rice against dicotyledonous harmful plants and/or sedges selected from the group consisting of carfentrazone, carfentrazone-ethyl, and benfuresate; and
      (B4) clefoxidim; and optionally, adjuvants or formulation auxiliaries conventionally used in crop protection.

2. The herbicidal composition of claim 1 which comprises the combination of (A) glufosinate or salts thereof and (B) carfentrazone-ethyl.

3. The herbicidal composition of claim 1 which comprises the combination of (A) glufosinate or salts thereof and (B) carfentrazone.

4. A method for controlling harmful plants in rice crops which comprises:
   applying an effective amount of a herbicide combination to the plants, seed of the plants, or the area under cultivation;
   wherein the herbicide combination comprises a synergistically effective amount of the composition of claim 1.

5. The method of claim 4,
   wherein the (B) herbicide is carfentrazone-ethyl.

6. The method of claim 4,
   wherein the (B) herbicide is carfentrazone.

7. The herbicidal composition of claim 1,
   which comprises the combination of (A) glufosinate salt and molinate.

8. The herbicidal composition of claim 1,
   which comprises the combination of (A) glufosinate salt and anilofos.

9. The herbicidal composition of claim 1,
   which comprises the combination of (A) glufosinate salt and oxadiazon.

10. The herbicidal composition of claim 1,
    which comprises the combination of (A) glufosinate salt and carfentrazone-ethyl.

11. The herbicidal composition of claim 1,
    which comprises the combination of (A) glufosinate salt and clefoxidim.

* * * * *